United States Patent [19]

Shimada et al.

[11] Patent Number: 4,927,959

[45] Date of Patent: May 22, 1990

[54] ALPRENOLOL DERIVATIVES

[75] Inventors: Shinichi Shimada, Utsunomiya; Noboru Kawaguchi; Tadayoshi Koyama, both of Ishibashi; Akinori Wakaiki, Ishibashi; Keiji Hayashi, Ishibashi; Yasuyoshi Takeshita; Masamichi Nakakoshi, both of Utsunomiya; Gosei Kawanishi, Ichikawa, all of Japan

[73] Assignee: Snow Brand Milk Products Co., Ltd., Sapporo, Japan

[21] Appl. No.: 239,663

[22] Filed: Sep. 2, 1988

[30] Foreign Application Priority Data

Sep. 4, 1987 [JP] Japan ................... 62-220268

[51] Int. Cl.$^5$ ............... C07C 69/353; C07C 69/593
[52] U.S. Cl. ..................... 560/193; 560/191; 560/204
[58] Field of Search ............ 560/193; 514/547

[56] References Cited

U.S. PATENT DOCUMENTS 4,515,974  5/1985  Zecher et al. ............... 560/193 X
4,810,697  3/1989  Speiser et al. ............... 560/193 X Primary Examiner—Werren B. Lone
Assistant Examiner—Vera C. Clarke
Attorney, Agent, or Firm—Oblon, Spivak, McClelland, Maier & Neustadt

[57] ABSTRACT

Novel alprenolol derivatives represented by the formula:

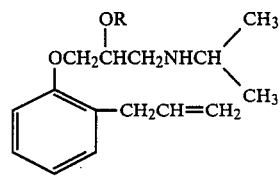

wherein R is

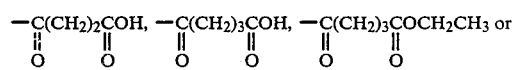

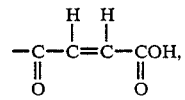

and hydrochlorides thereof are disclosed.

5 Claims, 14 Drawing Sheets

PLASMA LEVELS OF THE PARENT DRUG (ALPRENOLOL) AFTER ORAL ADMINISTRATION IN DOGS. (EQUIVALENT DOSE OF ALPRENOLOL HCl 20mg/kg, n=3~4)

THE RELATIONSHIP BETWEEN DOSE AND AUC (MEAN±S.D.)

ALPRENOLOL DERIVATIVES

BACKGROUND OF THE INVENTION

1. Field of the Invention

This invention relates to novel alprenolol derivatives for improving the so-called bioavailability of alprenolol as a β-blocking agent.

2. Description of the Prior Art

When alprenolol which is used as a β-blocking agent is orally administered, it has been known that the bioavailability of alprenolol in vivo is lowered because of being subjected to the first-pass effect of the liver similarly to other medicines. For example, it has been reported that the bioavailability of alprenolol is only 15% in the oral administration. Therefore, there is a problem that the concentration of alprenolol in blood is difficult to control.

It has been known that chemical modification as a means for preparing prodrug of the medicines. The method, however, has been intended to improve absorption of the medicines from gastrointestine [Clayton J. P. et al., J. Medicinal Chem., 18 (2), 172 (1975)] and is not a prodrug preparation to avoid the first-pass effect of the liver. The preparation of prodrug to evade the first-pass effect of the liver has not yet been reported of course on alprenolol, and on other various medicines.

SUMMARY OF THE INVENTION

An object of this invention is to provide an alprenolol derivative for improving the bioavailability of alprenolol by such a process that an orally administered alprenolol derivative is absorbed from digestive tract, distributed into blood without being affected by the first-pass effect of the liver and then converted to alprenolol.

The invention provides an alprenolol derivative represented by the following formula (I) and hydrochloride thereof:

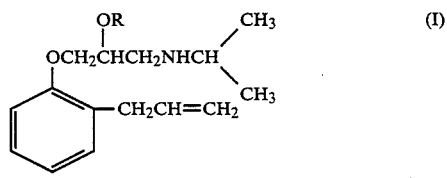

wherein R is

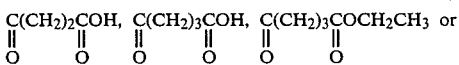

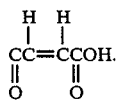

DESCRIPTION OF THE PREFERRED EMBODIMENTS

The alprenolol derivatives of this invention can be prepared by the reaction of alprenolol with succinic anhydride, glutaric anhydride or maleic anhydride to form an ester or by reacting alprenolol with glutaric anhydride to form an ester and further reacting with ethyl halide.

In addition, hydrochlorides of the alprenolol derivatives can be prepared by using alprenolol hydrochloride as a starting material and carrying out the same reaction as above.

Although the above ester may be formed by directly reacting the raw materials, it is usually preferred to carry out the reaction under reflux in the presence of a solvent, for example, toluene. The reaction is conducted for about 5 hours with stirring. The reaction mixture is allowed to cool and the solvent is distilled off. The resulting oily substance is purified by column chromatography to obtain the desired product.

In the above reaction, the above-mentioned cyclic anhydride of each aliphatic dicarboxylic acid is reacted to form an ester bond with a hydroxyl group which has a substitutable hydrogen as illustrated by the formula (I).

The IR absorption spectrum of alprenolol derivative (hydrochloride) in this invention, and mass spectrum and the Rf value of thin layer chromatography (abbreviated as TLC) of free alprenolol derivative are illustrated below.

Assuming the absorption and distribution of the derivatives in vivo, conversion tests to the parent drug (alprenolol) were carried out by the following method in buffer solutions having the pH of 2, 4 and 7.4.

Test method:

Britton-Robinson buffer solutions having the pH of 2, 4 and 7.4 were prepared. To each 800 μl of the buffer solution, 200 μl of an aqueous solution of each compound which had been adjusted to a concentration of 2 mg/ml were added. The resulting mixture was incubated at 37° C.

From each reaction mixture, 100 μl of sample were collected after 0, 1, 3, 5, 7 and 24 hours, diluted with a developer and subjected to high performance liquid chromatography (abbreviated as HPLC) under following conditions.

Figure 1:
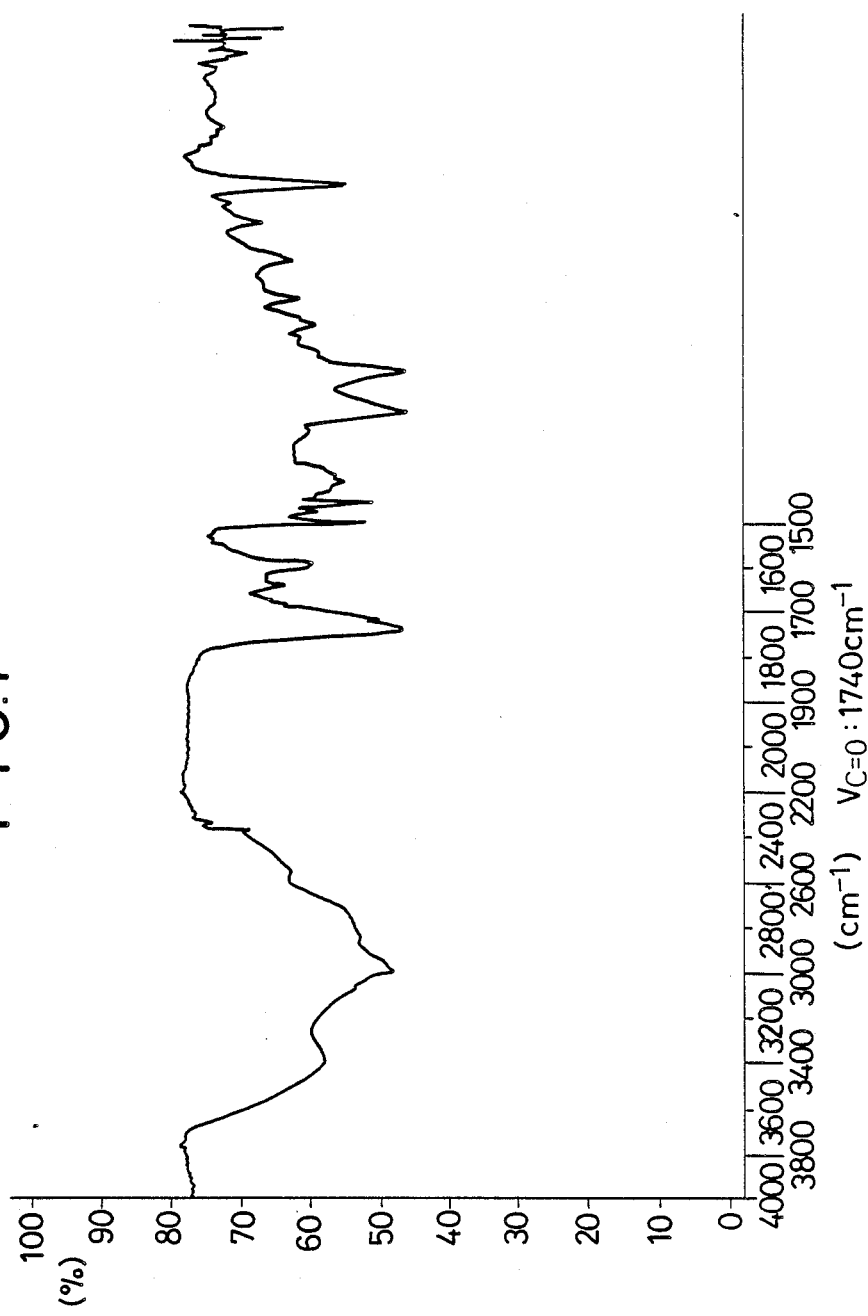
FIGS. 1 and 2 illustrate IR absorption spectrum and mass spectrum of the compound in Example 1, respectively.
Figure 2:
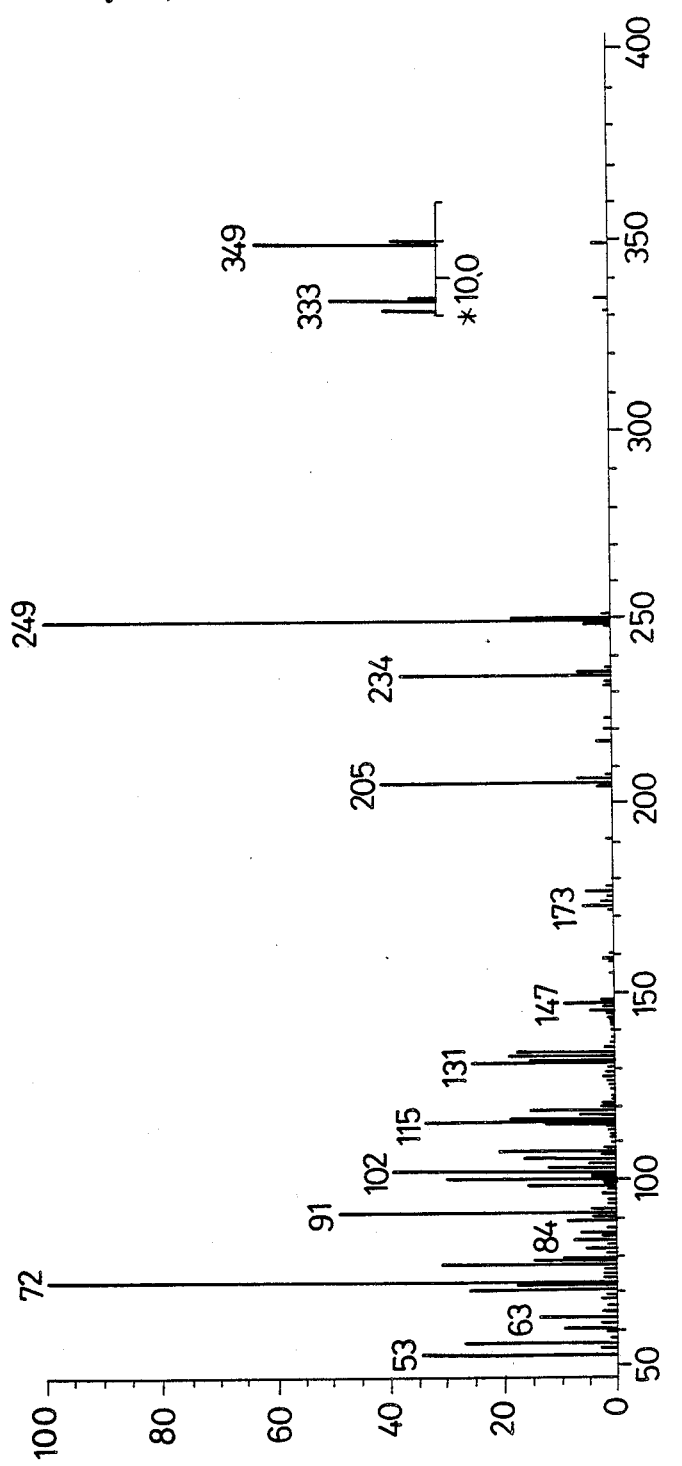
Figure 9:
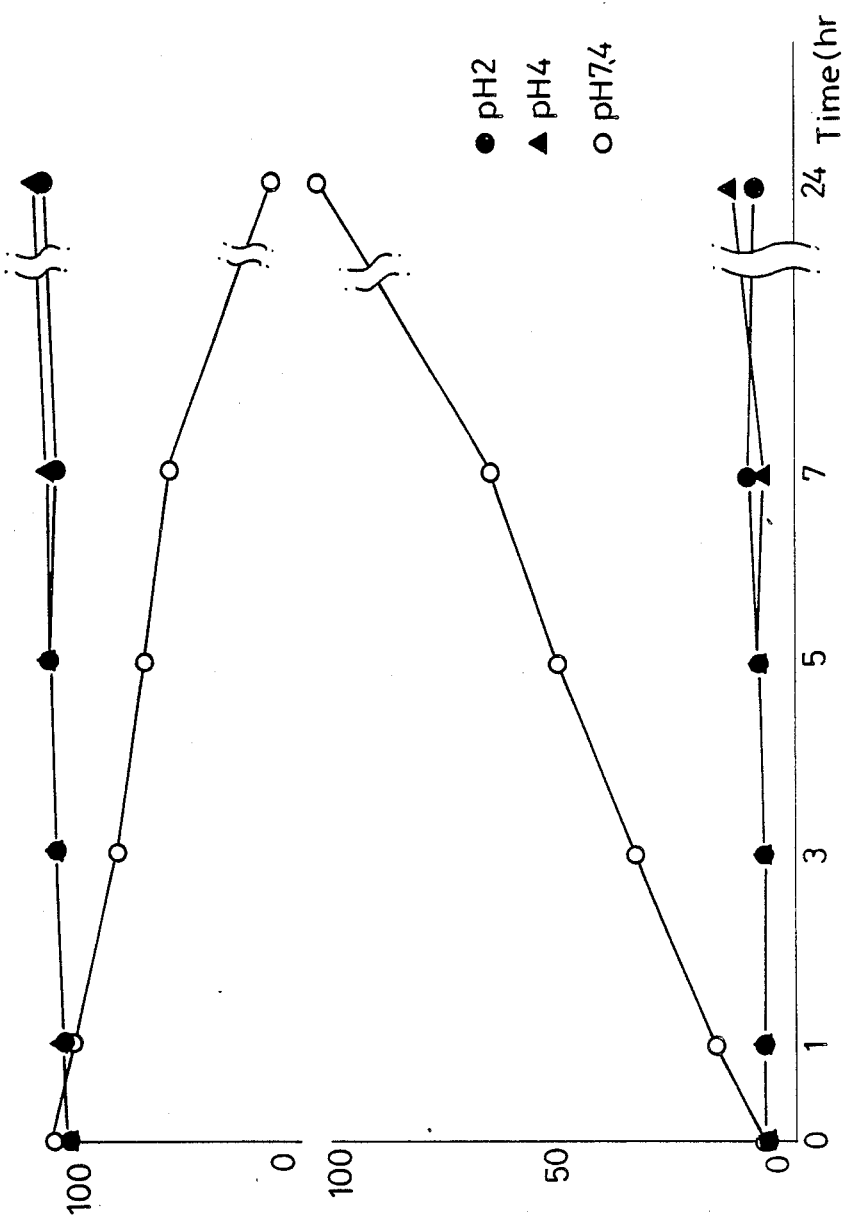
FIGS. 9 to 12 illustrate conversion of each of compounds (1) to (4) of Examples 1 to 3 and 5 in each of buffer solutions having pH of 2, 4, and 7.4.

(1) Butanedioic acid mono[1-{(2-allylphenoxy)methyl}{2-(1-methylethyl)amino}ethyl]ester and its hydrochloride (a) IR absorption spectrum; as illustrated in FIG. 1
(b) Mass spectrum; as illustrated in FIG. 2
(c) Rf value in TLC; 0.41
  Solvent system . . . CHCl₃:CH₃OH=5:1
  Color forming . . . UV Lamp (d) Conditions of HPLC in the conversion test;
Column...
  ODS 4.6φ×250 mm
  YMC-Pack A 303
Flow rate... 1 ml/min
Detector... UV Detector, Range 0.02
Eluent... $CH_3CN:CH_3OH:10$ mM $KH_2PO_4 = 2:3:5$
Detecting wave length... 270 nm
Retention time... 11.2 min Results are illustrated in FIG. 9.

Figure 3:
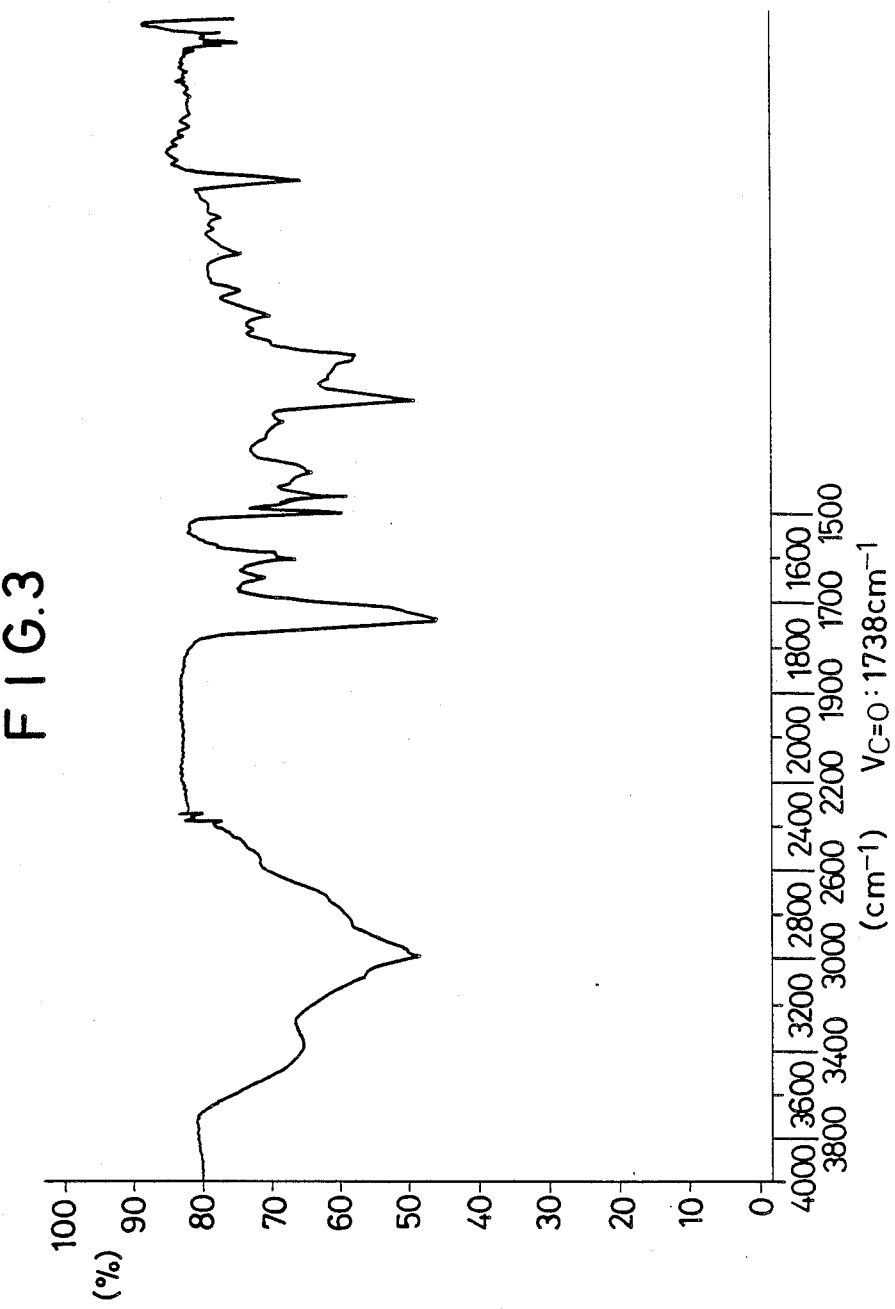
FIGS. 3 and 4 illustrate IR absorption spectrum and mass spectrum of the compound in Example 2, respectively.
Figure 4:
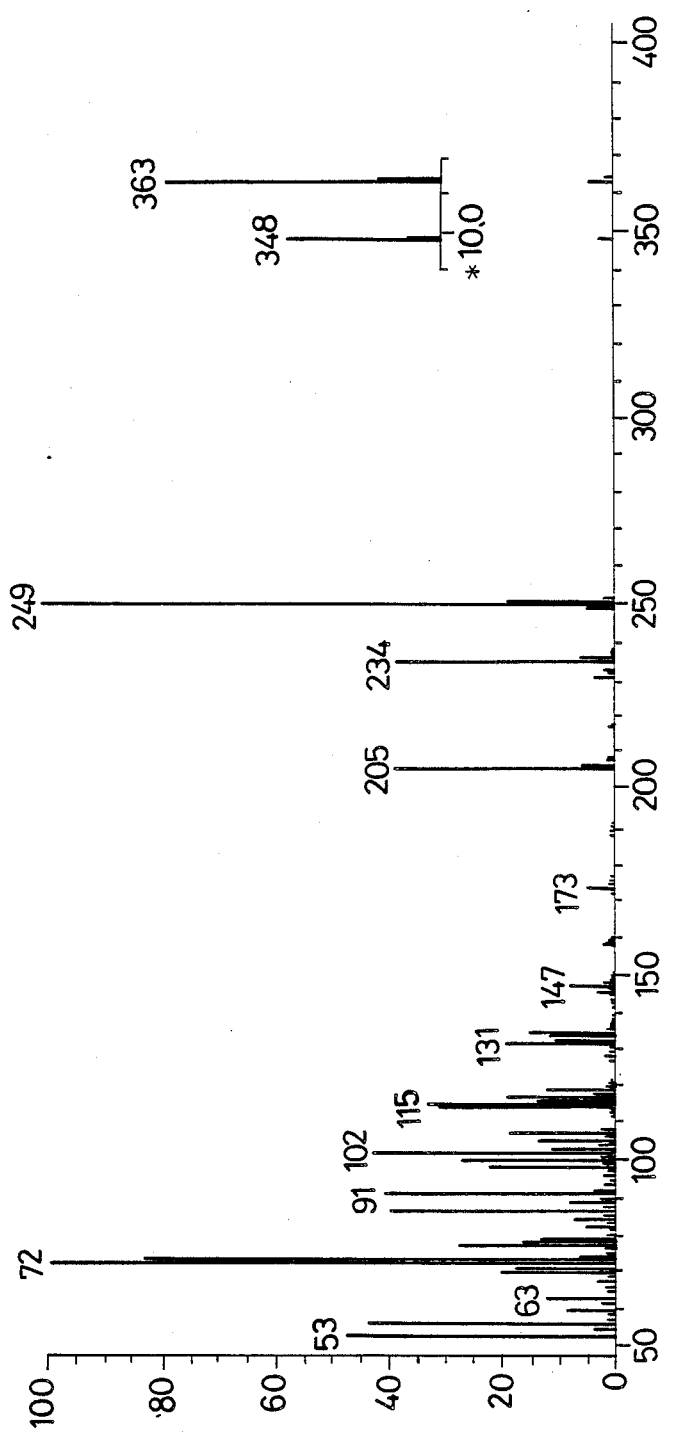
Figure 10:
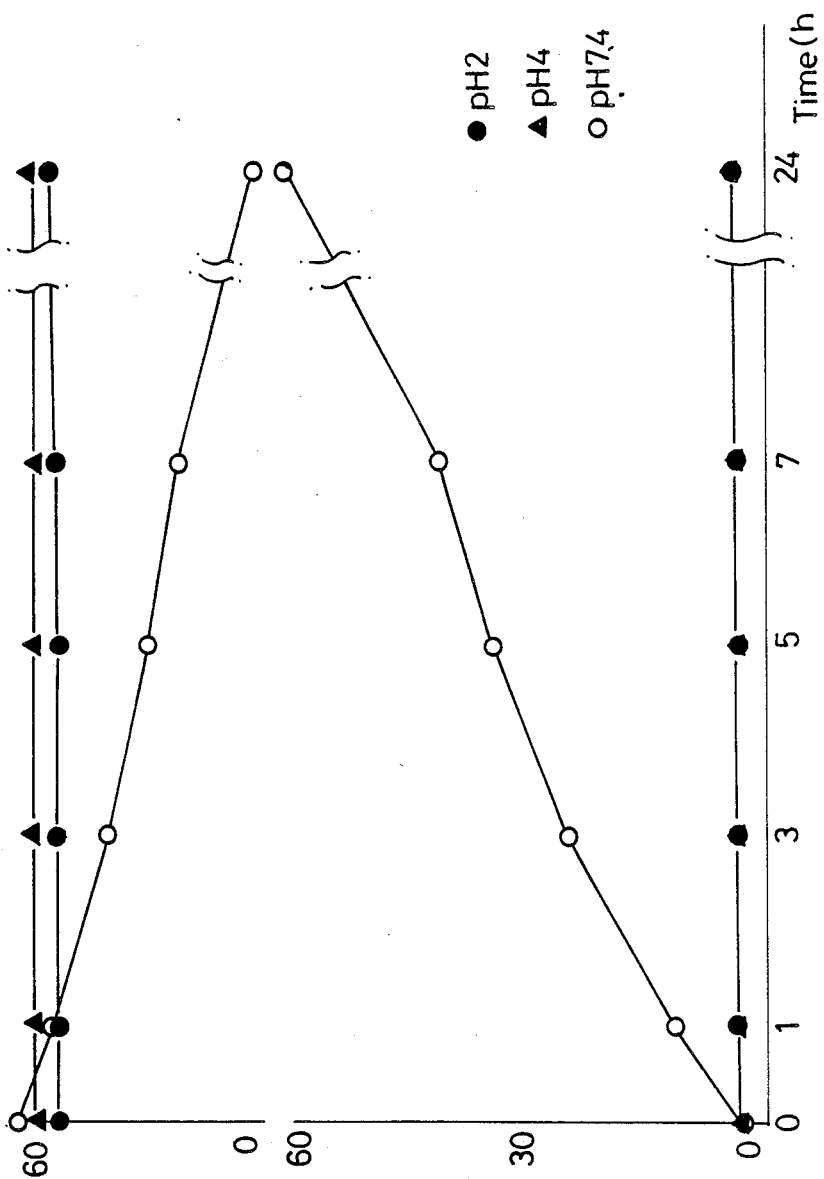

(2) Pentanedioic acid mono[1-{(2-allylphenoxy)methyl}{2-(1-(1-methylethyl)amino}ethyl]ester and its hydrochloride (a) IR absorption spectrum; as illustrated in FIG. 3
(b) Mass spectrum; as illustrated in FIG. 4
(c) Rf value in TLC; 0.38
  Solvent system... $CHCl_3:CH_3OH = 4:1$
  Detection... UV Lamp
(d) Conditions of HPLC in the conversion test;
Column...
  ODS 4.6φ×250 mm
  YMC-Pack A 303
Flow rate... 1 ml/min
Detector... UV Detector Range 0.02
Eluent... $CH_3CN:CH_3OH:10$ mM $KH_2PO_4 = 2:3:5$
Detecting wave length... 270 nm
Retention time... 11.8 min Results are illustrated in FIG. 10.

Figure 5:
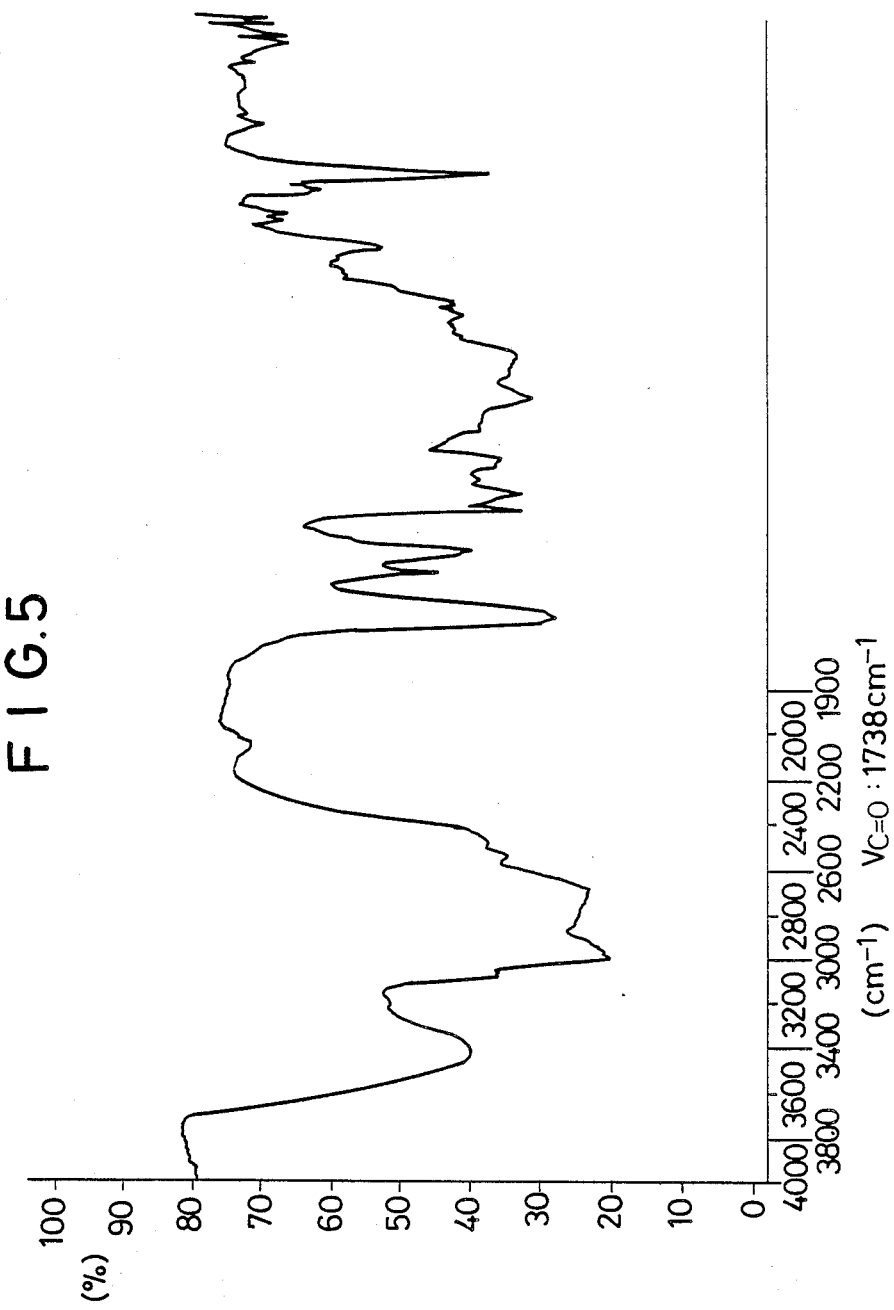
FIGS. 5 and 6 illustrate IR absorption spectrum and mass spectrum of the compound in Example 3, respectively.
Figure 6:
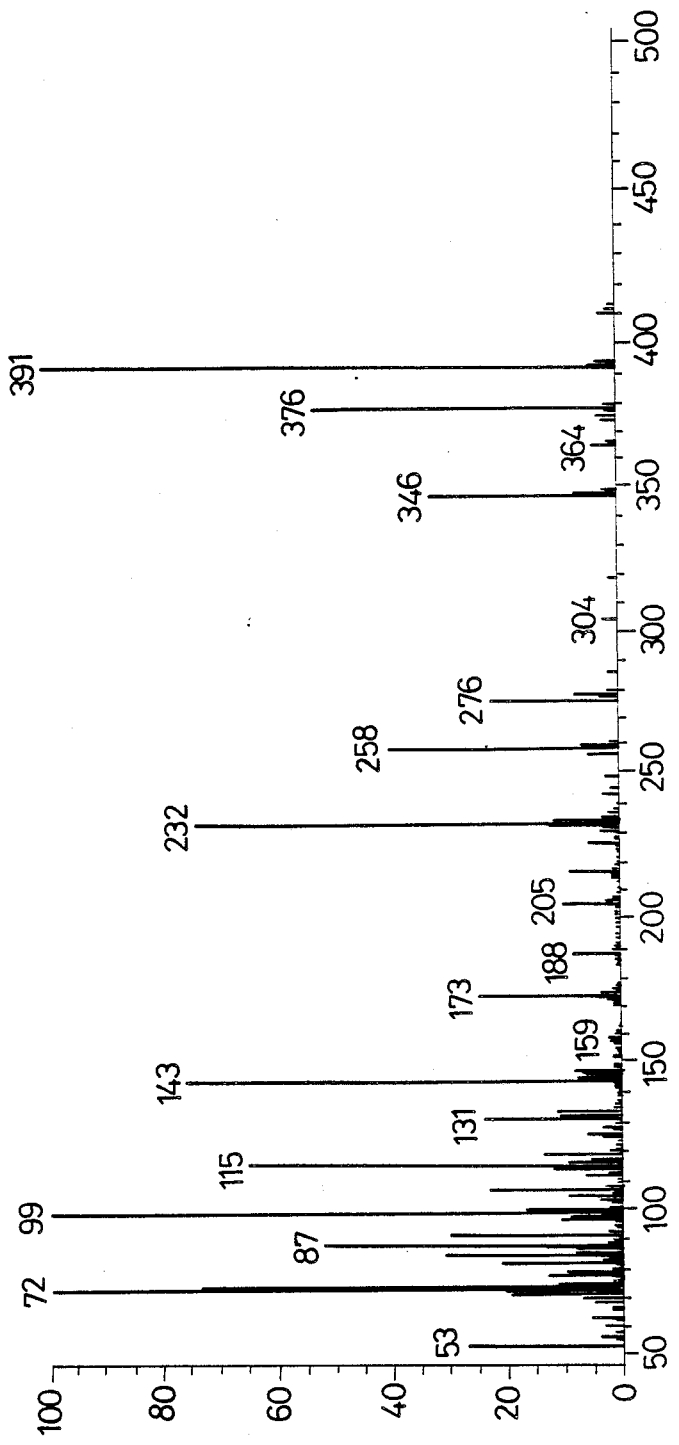
Figure 11:
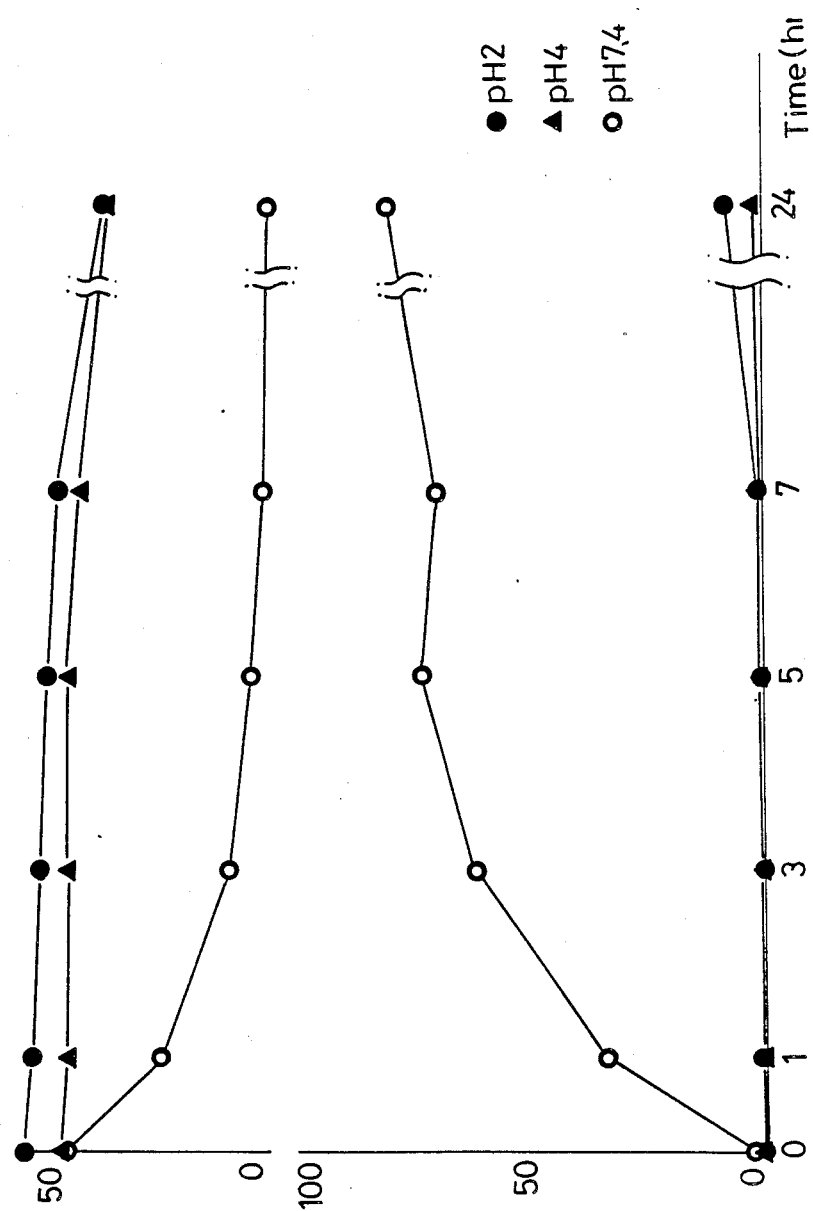

(3) 4-Ethoxycarbonylbutanoic acid mono[1-{(2-allylphenoxy)methyl}-{2-(1-methylethyl)amino}ethyl]ester and its hydrochloride (a) IR absorption spectrum; as illustrated in FIG. 5
(b) Mass spectrum; as illustrated in FIG. 6
(c) Rf value in TLC; 0.68
  Solvent system... $CHCl_3:CH_3OH = 7:1$
  Detection... UV Lamp
(d) Conditions of HPLC in the conversion test;
Column...
  ODS 4.6φ×250 mm
  YMC-Pack A 303
Flow rate... 1 ml/min
Detector... UV Detector Range 0.02
Eluent... $CH_3CN:CH_3OH:10$ mM $KH_2PO_4 = 1:1:1$
Detecting wave length... 270 nm
Retention time... 7.6 min Results are illustrated in FIG. 11.

Figure 7:
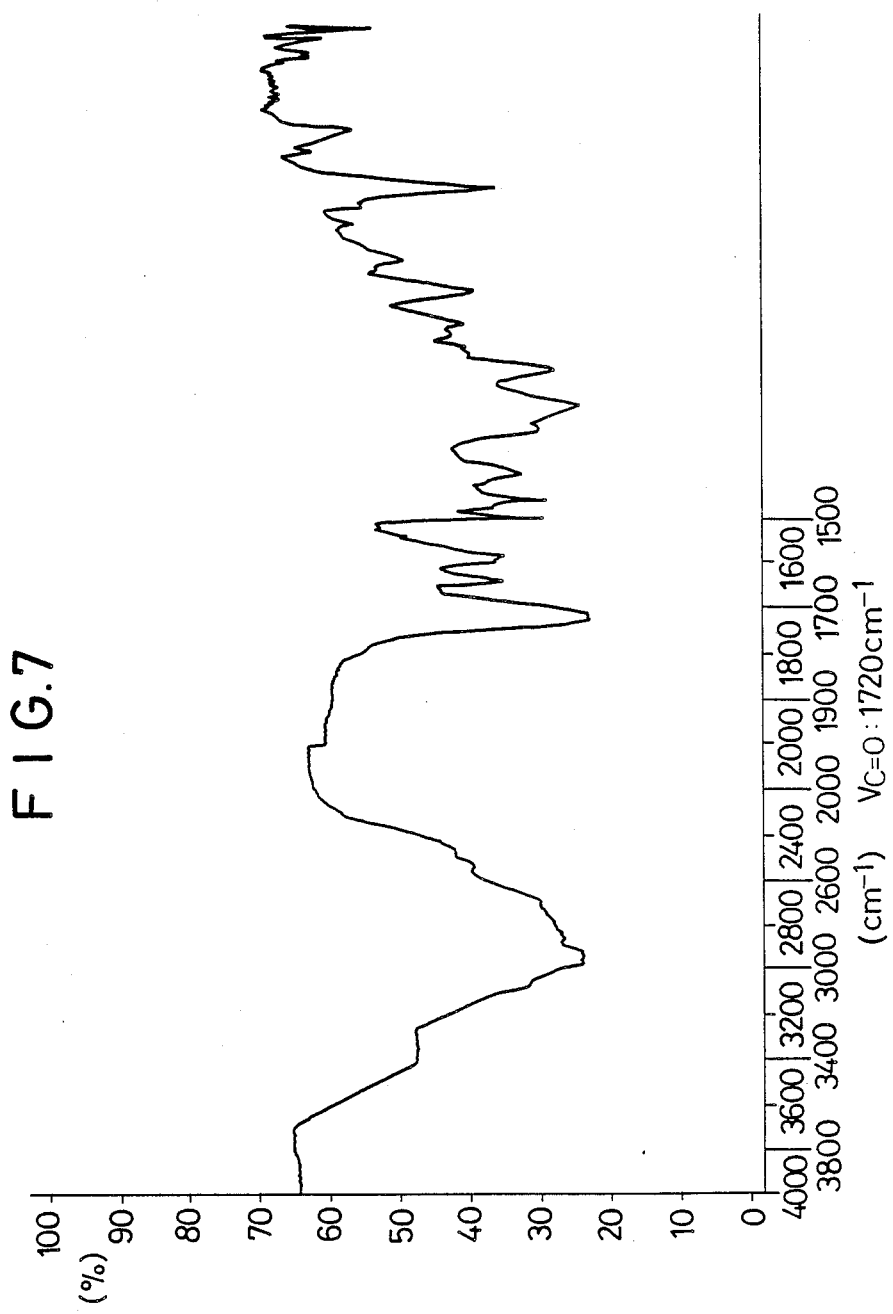
FIGS. 7 and 8 illustrate IR absorption spectrum and mass spectrum of the compound in Example 5, respectively.
Figure 8:
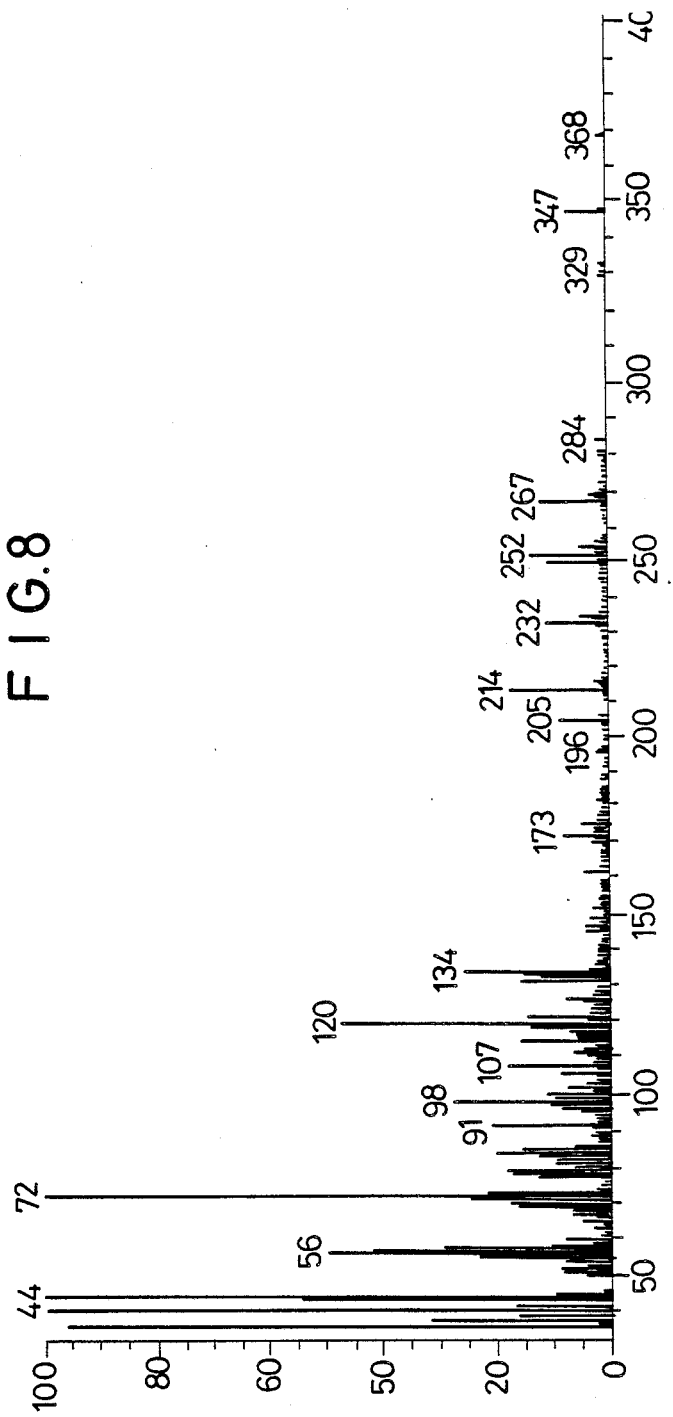
Figure 12:
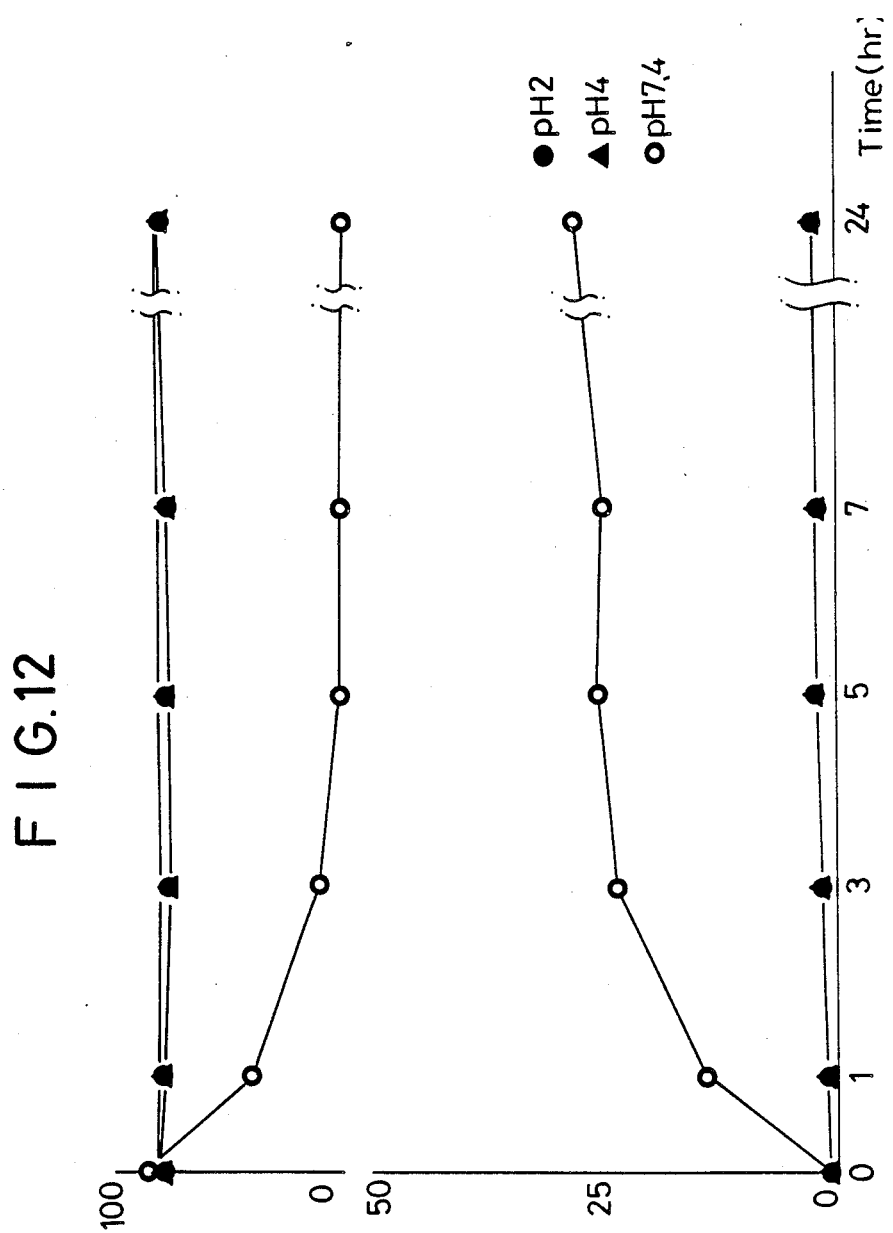

(4) (z)-Butenedioic acid mono[1-{(2-allylphenoxy)methyl}-{2-(1-methylethyl)amino}ethyl]ester and its hydrochloride (a) IR absorption spectrum; as illustrated in FIG. 7
(b) Mass spectrum; as illustrated in FIG. 8
(c) Rf value in TLC; 0.4
  Solvent system... $CHCl_3:CH_3OH = 4:1$
  Detection... UV Lamp
(d) Conditions of HPLC in the above conversion test;
Column...
  ODS 4.6φ×250 mm
  YMC-Pack A 303
Flow rate... 1 ml/min
Detector... UV Detector Range 0.02
Eluent... $CH_3CN:10$ mM $KH_2PO_4 = 1:2$
Detecting wave length... 270 nm
Retention time... 8.4 min Results are illustrated in FIG. 12.

As to the compounds (hydrochloride) described in the above (1)–(4), the conversion rate to the parent drug was examined in a buffer solution having the pH of 7.4 assuming blood pH. Table 1 illustrates half-life time (T ½) of each compound in the above buffer solution and 50% producing time (T' ½) of the parent drug in the same buffer solution.

TABLE 1

| Compound No. | Half-life time (T ½) | 50% producing time of the parent drug (T' ½) |
|---|---|---|
| (1) | 7.4 | 5 |
| (2) | 4.9 | 5 |
| (3) | 1.3 | 2 |
| (4) | 0.9 | 3 |

In the next step, the alprenolol drivative of this invention was orally administered to dogs as experimental animals. The results described below were obtained by investigating the improving effect on bioavailability.

Test method

Female beagle dogs (a body weight of about 10 kg) were used as the experimental animals. The 12 dogs were divided into 2 groups of 6 dogs and each group was alternately subjected to the experiment with intervals of 2 weeks. To the dogs, 2, 5, 10, 20 and 30 mg/kg of alprenolol hydrochloride 13.50 and 27.00 mg/kg of the compound (1) hydrochloride, (equivalent to 10, 20 mg/kg of the alprenolol hydrochloride, respectively) and 13.99 and 27.98 mg/kg of the compound (2) hydrochloride (equivalent to 10 and 20 mg/kg of alprenolol hydrochloride, respectively) were orally administered. Blood was collected respectively after 0.5, 1, 2, 4 and 6 hours. The plasma separated from the blood was extracted with ethanol. Plasma levels of the parent drug were determined by HPLC. The conditions for the HPLC analysis are shown as follows:

| Column | ODS 4.6φ × 250 mm YMC-Pack A-303 |
|---|---|
| Column Temperature | 30° C. |
| Flow rate | 0.8 ml/min |
| Detector | Fluorescence |
| Wave length | Excitation 271 nm Emission 315 nm |
| Eluent | $CH_3CN:CH_3OH:50$ mM $KH_2PO_4 = 2:3:5$ |

Figure 13:
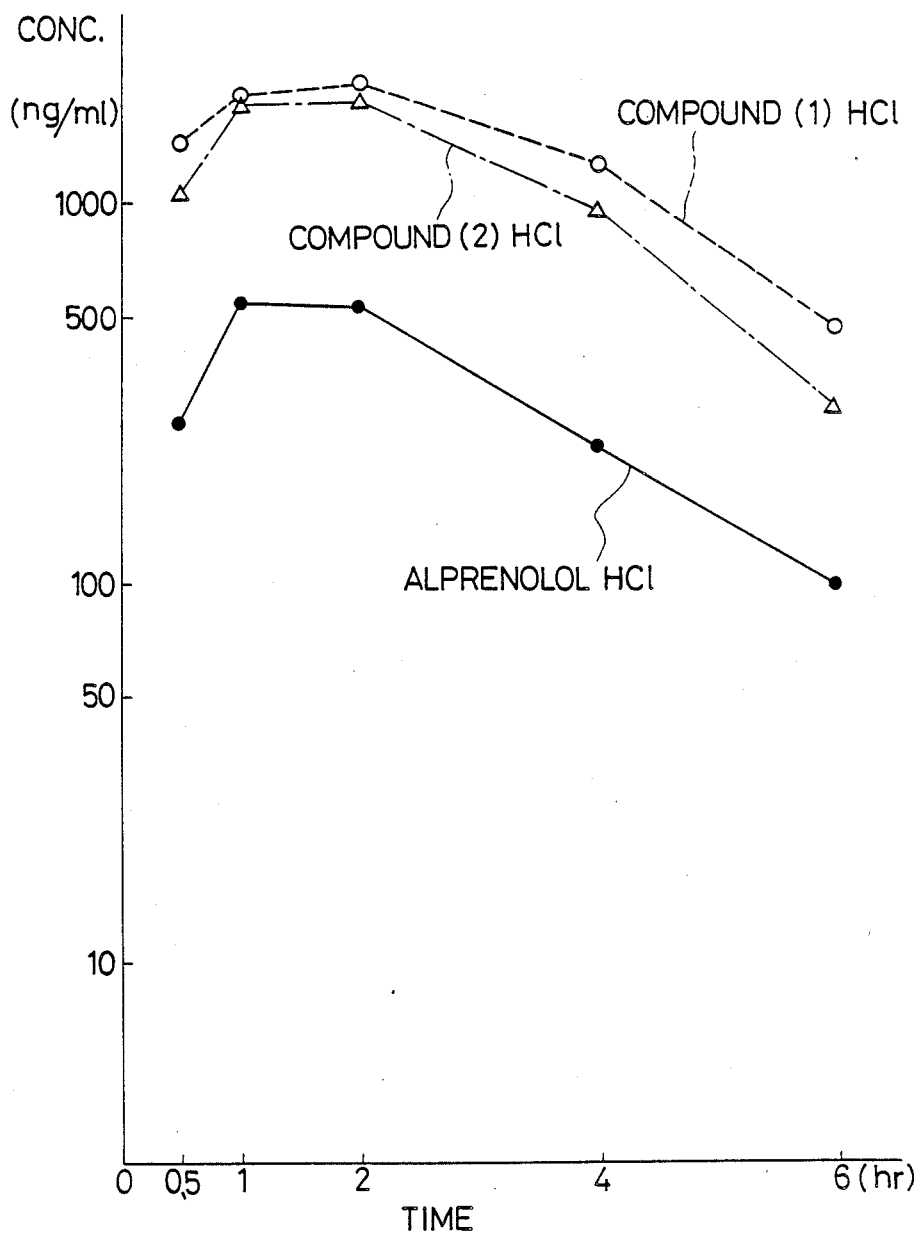
FIGS. 13 and 14 illustrate improving effect on the bioavailability of the alprenolol derivatives in this invention.
Figure 14:
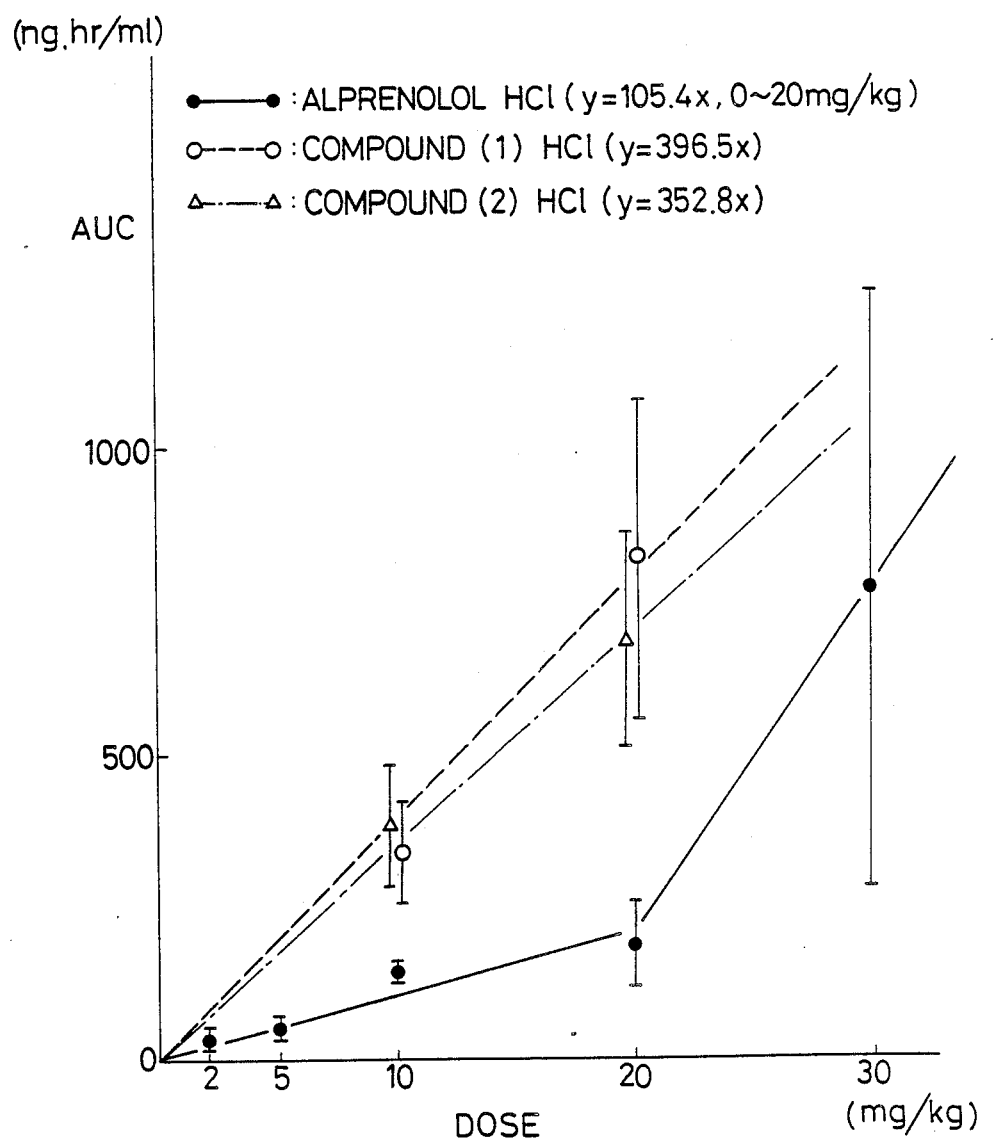

The results are shown in FIGS. 13 and 14. FIG. 13 shows plasma levels of alprenolol when 20 mg/kg of alprenolol hydrochloride and the dose equivalent thereto of the hydrochlorides of compounds (1) and (2) were administered. As shown in FIG. 13, significantly high plasma concentration of the parent drug are found after the administration of the hydrochlorides of compounds (1) and (2).

FIG. 14 shows the relationships between the doses and AUCs (area under the plasma concentration curves). In the case of alprenolol hydrochloride, the non-linear relationship with the threshold due to the first-pass effect is shown. On the other hand, the linear relationships are found in the hydrochlorides of compounds (1) and (2). This clearly illustrates that the bioavailability in the compounds of this invention is improved thereby contributing to avoid the first-pass effect.

Examples illustrating the preparation of the alprenolol derivatives of this invention will hereinafter be described in detail.

EXAMPLE 1

A mixture of 0.57 g of alprenolol hydrochloride as a β-blocking agent and 0.22 g of succinic anhydride was refluxed in the presence of 15 ml of toluene with stirring for 5 hours. The resultant reaction mixture was allowed to cool, and toluene was distilled off. The residual oily product was purified by column chromatography.

The product thus obtained was butanedioic acid mono[1-{(2-allylphenoxy)methyl}-{2-(1-methylethyl)amino}ethyl]ester hydrochloride. The amount was 0.7 g (91.0% yield).

FIG. 1 illustrates IR spectrum of this compound and has a characteristic absorption at 1740 cm$^{-1}$ due to the stretching vibration of C=O group. FIG. 2 illustrates mass spectrum of free base of the compound. The M$^+$ values is 349 and corresponds to the theoretical value.

EXAMPLE 2

A mixture of 1.5 g of alprenolol hydrochloride and 0.72 g of glutaric anhydride was refluxed in the presence of 30 ml of toluene with stirring for 5 hours. The resultant reaction mixture was allowed to cool, and toluene was distilled off. The residual oily product was purified by column chromatography.

The product thus obtained was pentanedioic acid mono[1-{(2-allylphenoxy)methyl}-{2-(1-methylethyl)amino}ethyl]ester hydrochloride. The amount was 1.95 g (92.9% yield).

FIG. 3 illustrates IR spectrum of this compound and has a characteristic absorption at 1738 cm$^{-1}$ due to the stretching vibration of C=O group. FIG. 4 illustrates mass spectrum of free base of the compound. The M$^+$ value is 363 and corresponds to the theoretical value.

EXAMPLE 3

A mixture of 1.1 g of alprenolol hydrochloride and 0.53 g of glutaric anhydride was refluxed in the presence of toluene for 5 hours. The resultant reaction mixture was allowed to cool and toluene was distilled off. The residual oily substance was dissolved in water and the pH was adjusted to 10.0 by adding an aqueous sodium hydroxide solution. The resultant aqueous solution was washed with ether, adjusted the pH to 5.0–5.5 and extracted with dichloromethane. The organic solvent layer was separated and dichloromethane was distilled off to obtain 1.5 g of oily product. The oily product was dissolved in dimethylformamide. To the resultant solution, 0.6 g of anhydrous potassium carbonate and 0.8 g of ethyl iodide were added and the resultant mixture was reacted at 40°–50° C. for 4 hours with stirring. The reaction mixture thus obtained was concentrated, mixed with water and extracted with ether. The ether layer was concentrated to obtain oily product. The oily product was mixed again with ether and hydrogen chloride gas was bubbled into the solution obtained. Purification was carried out by column chromatography. The product thus obtained was 4-ethoxycarbonylbutanoic acid mono[1-{(2-allylphenoxy)methyl}-{2-(1-methylethyl)amino}ethyl]ester hydrochloride. The amount was 0.45 g (27.3% yield).

FIG. 5 illustrates IR spectrum of this compound and has a characteristic absorption at 1738 cm$^{-1}$ due to the stretching vibration of C=O group. FIG. 6 illustrates mass spectrum of free base of the compound. The M$^+$ value is 391 and corresponds to the theoretical value.

EXAMPLE 4

A mixture of 1.5 g of alprenolol hydrochloride and 0.72 g of glutaric anhydride was refluxed in the presence of 30 ml of toluene with stirring for 5 hours. The resultant reaction mixture was allowed to cool and toluene was distilled off. The residual oily product was purified by column chromatography.

The product thus obtained was pentanedioic acid mono[1-{(2-allylphenoxy)methyl}-{2-(1-methylethyl)amino}ethyl]ester hydrochloride. The amount was 1.95 g (92.9% yield).

Then 1.5 g of thus obtained pentanedioic acid mono[1-{(2-allylphenoxy)methyl}-{2-(1-methylethyl)amino}ethyl]ester hydrochloride were dissolved in 10 ml of ethanol. A small amount of dry hydrogen chloride gas was bubbled into the resultant solution. The solution was stored for 24 hours at room temperature in the sealed state.

After distilling off ethanol, chloroform was added to the residue in order to remove hydrogen chloride gas and distilled off again.

The resultant residue was dissolved in a small amount of chloroform, and purified by column chromatography.

The product thus obtained was 4-ethoxycarbonylbutanoic acid mono[1-{(2-allylphenoxy)methyl}-{2-(1-methylethyl]amino}ethyl ester hydrochloride. The amount was 0.35 g (21.8% yield).

EXAMPLE 5

A mixture of 0.45 g of alprenolol hydrochloride and 0.2 g of maleic anhydride was refluxed in toluene with stirring for 5 hours. The resultant reaction mixture was allowed to cool, and toluene was distilled off. The residual oily product was fractionated by column chromatography and was purified by liquid chromatography.

The product thus obtained was (z)butenedioic acid mono[1-{(2-allylphenoxy)methyl}-{2-(1-methylethyl)amino}ethyl]ester hydrochloride. The amount was 0.085 g (14.1% yield).

FIG. 7 illustrates IR spectrum of this compound and has a characteristic absorption at 1720 cm$^{-1}$ due to the stretching vibration of C=O group. FIG. 8 illustrates mass spectrum of free base of the compound. The M$^+$ value is 347 and corresponds to the theoretical value.

What is claimed is:

1. An alprenolol derivative of the formula:

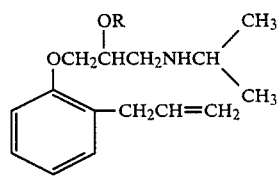

wherein R is $$-\underset{\underset{O}{\|}}{C}(CH_2)_2COH, \quad -\underset{\underset{O}{\|}}{C}(CH_2)_3COH, \quad -\underset{\underset{O}{\|}}{C}(CH_2)_3COCH_2CH_3 \text{ or}$$

-continued

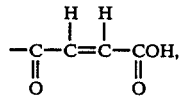

and a hydrochloride thereof.

2. Butanedioic acid mono[1-{(2-allylphenoxy)methyl}-{2-(1-methylethyl)amino}ethyl]ester and the hydrochloride thereof.

3. Pentanedioic acid mono[1-{(2-allylphenoxy)methyl}-{2-(1-methylethyl)amino}ethyl]ester and the hydrochloride thereof.

4. 4-Ethoxycarbonylbutanoic acid mono[1-{(2-allylphenoxy)methyl}-{2-(1-methylethyl)amino}ethyl]ester and the hydrochloride thereof.

5. (z)Butenedioic acid mono[1-{(2-allylphenoxy)methyl}-{2-(1-methylethyl)amino}ethyl]ester and the hydrochloride thereof.

* * * * *